(12) United States Patent
Kerl et al.

(10) Patent No.: US 10,293,191 B2
(45) Date of Patent: May 21, 2019

(54) HAIR-CONDITIONING AGENT AND METHOD FOR OXIDATIVE HAIR DYEING WITH IMPROVED BRIGHTENING PERFORMANCE

(71) Applicant: Henkel AG & Co. KGaA, Duesseldorf (DE)

(72) Inventors: Sylvia Kerl, Hamburg (DE); Susanne Bietz, Elmshorn (DE); Thomas Hippe, Appen (DE); Hartmut Manneck, Barnitz (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 11 days.

(21) Appl. No.: 15/654,711

(22) Filed: Jul. 20, 2017

(65) Prior Publication Data
US 2018/0021601 A1    Jan. 25, 2018

(30) Foreign Application Priority Data
Jul. 22, 2016    (DE) .......................... 10 2016 213 441

(51) Int. Cl.
| | |
|---|---|
| *A61Q 5/10* | (2006.01) |
| *A61K 8/06* | (2006.01) |
| *A61K 8/22* | (2006.01) |
| *A61K 8/34* | (2006.01) |
| *A61K 8/36* | (2006.01) |
| *A61K 8/41* | (2006.01) |
| *A61K 8/362* | (2006.01) |
| *A61K 8/65* | (2006.01) |

(52) U.S. Cl.
CPC ................ *A61Q 5/10* (2013.01); *A61K 8/062* (2013.01); *A61K 8/22* (2013.01); *A61K 8/34* (2013.01); *A61K 8/361* (2013.01); *A61K 8/362* (2013.01); *A61K 8/41* (2013.01); *A61K 8/416* (2013.01); *A61K 8/65* (2013.01); *A61K 2800/882* (2013.01)

(58) Field of Classification Search
CPC ... A61Q 5/10; A61K 8/22; A61K 8/34; A61K 8/361; A61K 8/362; A61K 8/65; A61K 8/41
See application file for complete search history.

(56) References Cited

U.S. PATENT DOCUMENTS

| | | | |
|---|---|---|---|
| 2003/0106167 A1* | 6/2003 | Rose | A61K 8/411 8/405 |
| 2003/0150069 A1 | 8/2003 | Kleen et al. | |
| 2006/0277695 A1* | 12/2006 | Kleen | A61K 8/416 8/405 |
| 2008/0262085 A1 | 10/2008 | Kainz et al. | |
| 2011/0138545 A1* | 6/2011 | Legrand | A61K 8/44 8/407 |
| 2017/0165161 A1 | 6/2017 | Manneck et al. | |

FOREIGN PATENT DOCUMENTS

| | | |
|---|---|---|
| CN | 105168016 A | 12/2015 |
| DE | 10051774 A1 | 4/2002 |
| EP | 1174112 A2 | 1/2002 |
| WO | 2016100258 A1 | 6/2016 |

OTHER PUBLICATIONS

Product catalog of Seiwa Kasei (Hydrolyzed Protein; Peptide and Its Derivatives) dated Sep. 14, 2015.*
Intellectual Property Office, Search Report under Section 17(5) for United Kingdom Patent Application No. GB1711572.6 dated Mar. 29, 2018.

* cited by examiner

*Primary Examiner* — Eisa B Elhilo
(74) *Attorney, Agent, or Firm* — Lorenz & Kopf, LLP

(57) ABSTRACT

Coloring agents for keratin fibers and methods for the oxidative dyeing of keratin fibers are provided herein. In an embodiment, a coloring agent for keratin fibers includes, based on its weight, a) at least one compound selected from the group of oxidation dye precursors, direct dyes, or mixtures thereof, b) at least one dicarboxylic acid having 2 to 10 carbon atoms and/or at least one salt of this/these acid(s) in a total quantity of from about 0.1 to about 5% by weight, calculated respectively on the undissociated dicarboxylic acid and based on the weight of the coloring agent, c) at least one keratin hydrolyzate having an average molecular weight Mw in the range from about 2000 to about 7000 daltons, d) from about 20 to about 95% by weight of water and e) from zero to less than about 0.1% by weight of peroxide compound(s).

20 Claims, No Drawings

HAIR-CONDITIONING AGENT AND METHOD FOR OXIDATIVE HAIR DYEING WITH IMPROVED BRIGHTENING PERFORMANCE

CROSS-REFERENCE TO RELATED APPLICATION

This application claims priority to German Patent Application No. 10 2016 213 441.8, filed Jul. 22, 2016, which is incorporated herein by reference in its entirety.

TECHNICAL FIELD

The present disclosure relates to a hair-conditioning agent for oxidative hair dyeing and to a gentle method for oxidative hair dyeing in which keratin fibers are protected from oxidative influences or oxidative hair damage is repaired.

BACKGROUND

The oxidative dyeing of hair can lead to damage to the keratin fiber due to the aggressive agents. In particular, the natural hydrophobicity of the keratinic fiber is reduced since the coloring agents first have to penetrate the hair in order to develop their effect. However, the water-repellent effect is, on the one hand, a natural protection of the hair; on the other hand, desirable parameters such as gloss, suppleness, grip and "springing" of the hair are closely linked to it.

In order to overcome these disadvantages, so-called pre-treatment agents are on the market which are intended to protect the hair from the aggressive influence. However, these often damage the hair or impair the success of the subsequent lightening or dyeing of the hair. In particular, the washing fastness of the dyeing may be impaired by the pretreatment agent. Numerous post-treatment agents are also known for the purpose of repairing the hair damage caused by the oxidative dyeing treatment. However, all of these methods require a multi-stage application method, either an application of a further hair treatment agent before or after the dyeing. This is often perceived as cumbersome by the consumer, since even the oxidative dyeing treatment itself, with several working steps and an exposure time of up to 60 minutes, requires much effort.

The object of the present disclosure was to provide an agent and a method for oxidative hair dyeing with a hair-protecting treatment which overcomes the mentioned disadvantages without adversely affecting the color result of the oxidative dyeing treatment. In particular, a coloring agent and a method are provided in which the hair is not burdened and as little hair damage as possible occurs. Furthermore, the achieved hair protection should consume as little time as possible and, if possible, occur together with the dyeing step itself.

The use of dicarboxylic acids such as succinic acid in hair care is state of the art. These are widely used in shampoos and in particular in conditioners in order to develop care effects there. Thus, patent application WO 2005/115314A1 discloses a method for the restructuring of keratin fibers in which the keratin fibers are brought into contact with cystine and with at least one dicarboxylic acid having 2 to 10 carbon atoms, wherein preferred dicarboxylic acids are selected from oxalic acid, malonic acid, succinic acid, glutaric acid, adipic acid, pimelic acid, azelaic acid, maleic acid, fumaric acid and sorbic acid and succinic acid is particularly preferred. The patent application DE 10051774 A1 describes the use of short-chain carboxylic acids with a molecular weight below 750 g/mol in cosmetic agents as an active ingredient for the restructuring of keratin fibers. Patent application EP1174112A discloses hair treatment agents which, in addition to an organic acid, contain an organic solvent, a cationic surfactant and a higher alcohol as further mandatory constituents, and which serve to repair pores in hair.

Recently, agents have also been offered in the market to which dyeing compositions are to be admixed and contain dicarboxylic acids for the purpose of fiber protection. In the case of the compositions mentioned, there is no application of a further hair treatment agent before or after the dyeing, however, the agent must be mixed with the actual coloring agent before application, which also means a further work step and is considered cumbersome by the consumer.

BRIEF SUMMARY

Coloring agents for keratin fibers and methods for the oxidative dyeing of keratin fibers are provided herein. In an embodiment, a coloring agent for keratin fibers includes, based on its weight,
a) at least one compound selected from the group of oxidation dye precursors, direct dyes, or mixtures thereof,
b) at least one dicarboxylic acid having 2 to 10 carbon atoms and/or at least one salt of this/these acid(s) in a total quantity of from about 0.1 to about 5% by weight, calculated respectively on the undissociated dicarboxylic acid and based on the weight of the coloring agent,
c) at least one keratin hydrolyzate having an average molecular weight Mw in the range from about 2000 to about 7000 daltons,
d) from about 20 to about 95% by weight of water and
e) from zero to less than about 0.1% by weight of peroxide compound(s).

In another embodiment, a method for the oxidative dyeing of keratin fibers includes the following method steps:
I. Providing a composition (A) comprising, based on its weight,
a) at least one compound selected from the group of oxidation dye precursors, direct dyes, and mixtures thereof,
b) at least one dicarboxylic acid having 2 to 10 carbon atoms and/or at least one salt of these acid(s) in a total quantity of from about 0.1 to about 5% by weight, calculated respectively on the undissociated dicarboxylic acid and based on the weight of the composition (A),
c) at least one keratin hydrolyzate having an average molecular weight Mw in the range from about 2000 to about 7000 daltons,
d) from about 20 to about 95% by weight of water, and
e) zero to less than about 0.1% by weight of peroxide compound(s),
II. Providing a composition (B) comprising at least one peroxide compound, in an amount of from about 1 to about 23% by weight, based respectively on the weight of the composition (B), wherein the composition (B) has a pH value in the range of from about 2.5 to about 6.5,
III. Mixing the compositions (A) and (B) with each other, directly afterward
IV. Applying the mixture of (A) and (B) to the keratin fibers, and
V. Rinsing after an exposure time of from about 0.1 to about 60 minutes,
VI. Optionally one or more of shaping, conditioning and/or drying the hair.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has now been found that oxidative coloring agents with improved fiber protection can be provided when the dye cream to be mixed with the developer in the course of the preparation by the customer contains, in addition to typical constituents such as water and dyes, or their precursors, at least one dicarboxylic acid having from about 2 to about 10 carbon atoms and is largely free of peroxides. Not only is a further working step thereby avoided, but these agents are also more effective in the protection of fibers when the dicarboxylic acid(s) are otherwise used in the same way as the subsequent admixture.

The oxidation dye precursors (ODP) and alkalizing agents present in oxidative coloring agents are usually incorporated into a cosmetically suitable carrier, for example a cream, a gel or a surfactant-containing solution. The carrier ensures a homogeneous distribution of the coloring agent on the hair. Thin-liquid carriers should be thickened for a sufficient residence time before application.

Commercial oxidation coloring agents are usually formulated in product series which comprise a standardized carrier which can be combined as unrestrictedly as possible with the nuance-specific ODP combination and alkalizing agents.

Consumers can usually find out about the achievable dyeing of the hair in a note on the coloring agent package and/or a color card accompanying the package. It is therefore very important for the consumer that the result of the dyeing match the color specified by the manufacturer as precisely as possible.

The result of the dyeing depends not only on the combination of the ODP and, if appropriate, the direct dyes (DD), but is also influenced by the ingredients of the carrier. For example, the dyes formed or directly used during the course of the color development under the influence of the oxidizing agent can have a distinctly different absorption capacity on the fiber; the carrier ingredients can also have a different effect on each dye.

Hair coloring agents are therefore tested comprehensively and with effort before market introduction for the color which can be achieved as well as for a variety of application properties. These tests therefore take into account the interactions between the ODP and the carrier only for a specific carrier. On the part of manufacturers, there is a regular desire to tailor a hair coloring agent series specifically to the special needs of certain consumer groups by adding corresponding active or care agents to the standardized carrier. For consumers with more severely damaged hair, for example, the addition of one or more care agents with hair-repairing effect would be recommended; for consumers with fine hair, the addition of one or more active ingredients strengthening the hair structure would be recommended, while adding too much conditioning agent would further damage the hair.

The addition of such additives, however, can lead to differences between the additive-free (standard) carrier and the targeted hair dye with the additive carrier. Such color differences are referred to as "color shifts" in the sense of the present application. This color shift, also referred to as dE or $\Delta E$, can be measured colorimetrically well with a color measuring device, with which the colors in the L*, a*, b* color space are measured, for example, with a color measuring device from Datacolor, type Spectraflash 450.

The L*, a*, b* color space is understood to be the CIELAB color space. The L-value stands for the brightness of the dyeing (black-white-axis); the greater the value for L, the brighter the dyeing. The a-value stands for the red-green axis of the system; the greater this value, the more the dyeing is shifted to red. The b-value stands for the yellow-blue axis of the system; the larger this value, the more the dyeing is shifted to the yellow.

The color shift $\Delta E$, i.e., the color difference between two (hair) colors, for which an L*, a*, b* value combination was determined, is calculated according to the following formula:

$$\Delta E = ((L_i - L_0)^2 + (a_i - a_0)^2 + (b_i - b_0)^2)^{1/2}$$

The larger the value for $\Delta E$, the more pronounced the color difference or "color shift". Color differences with $\Delta E < 2$ are visible to the trained eye. Color differences with $\Delta E > 2$ are also visible ro the untrained eye.

In the worst case, the addition of an additive to a coloring agent carrier causes a color shift to the additive-free carrier (standard) with $\Delta E > 2$, which is also visible to the untrained eye of the consumer. In order to avoid having to perform elaborate tests with regard to the achievable hair coloring and possibly the fastness properties with each change in the additive of the standard carrier, it is therefore desirable to identify active and care substances for the hair whose addition causes no or at least only a slight color shift. In the case of bright color nuances, the lifting performance or brightening performance L is the main focus; shifts of the color parameters a* or b* play a subordinate role. The present disclosure was therefore based on the object of providing a method for oxidative hair dyeing in which one or more selected care and active ingredients are used which have no or only a minimal color shift or no or only a minimal loss of lifting performance or brightening performance L.

The present disclosure is based on the observation that oxidative coloring agents with an addition of at least one dicarboxylic acid having from about 2 to about 10 carbon atoms and/or at least one salt of these acids in a total amount of from about 0.1 to about 5% by weight, calculated respectively on the undissociated dicarboxylic acid and, based on the weight of the peroxide-free coloring agent, optionally in combination with at least one basic amino acid selected from arginine, lysine and histidine, cause reduced hair damage but, under the same oxidation conditions, have a lower brightening performance ("lifting performance") and lead to a darker color result.

Surprisingly, it has been found that an oxidative hair coloring agent could be improved in terms of its care properties by the addition of at least one dicarboxylic acid having from about 2 to about 10 carbon atoms, optionally in combination with at least one basic amino acid selected from arginine, lysine and histidine, without deviating from the targeted hair color in a manner which is perceptible to the human eye with respect to the brightening performance ("lifting performance") of the targeted hair dyeing with the original hair coloring agent without dicarboxylic acid having from about 2 to about 10 carbon atoms and without basic amino acids selected from arginine, lysine and histidine, if at least one keratin hydrolyzate with an average molecular weight Mw is also contained in the range from about 2000 to about 7000 dalton, preferably in the range from about 3000 to about 5000 dalton.

The subject of the present disclosure provides, in a first embodiment, coloring agents for keratin fibers, in particular for human hair, containing, based on their weight,
a) at least one compound selected from the group of oxidation dye precursors and direct dyes, and mixtures thereof,
b) at least one dicarboxylic acid having from about 2 to about 10 carbon atoms and/or at least one salt of this/these acid(s) in a total quantity of from about 0.1 to about 5% by weight, calculated respectively on the undissociated dicarboxylic acid and based on the weight of the coloring agent, c) at least one keratin hydrolyzate having an average molecular weight Mw in the range from about 2000 to about 7000 daltons, preferably in the range from about 3000 to about 5000 daltons, d) from about 20 to about 95% by weight of water and e) from zero to less than about 0.1% by weight of peroxide compound(s).

An additional subject of the present disclosure is a method for the oxidative dyeing of keratin fibers, in particular of human hair, which comprises the following method steps I. Providing a composition (A) containing, based on its weight, a) at least one compound selected from the group of oxidation dye precursors and direct dyes, and mixtures thereof, b) at least one dicarboxylic acid having from about 2 to about 10 carbon atoms and/or at least one salt of this/these acid(s) in a total quantity of from about 0.1 to about 5% by weight, calculated respectively on the undissociated dicarboxylic acid and based on the weight of the composition (A), c) at least one keratin hydrolyzate having an average molecular weight Mw in the range from about 2000 to about 7000 daltons, preferably in the range from about 3000 to about 5000 daltons, d) from about 20 to about 95% by weight of water and e) zero to less than about 0.1% by weight of peroxide compound(s).

II. Providing a composition (B) containing at least one peroxide compound, which preferably is hydrogen peroxide in an amount of from about 1 to about 23% by weight, further preferably from about 2.5 to about 2% by weight, particularly preferably from about 4 to about 20% by weight, very particularly preferably from about 5 to about 18% by weight and most preferably from about 6 to about 12% by weight, based respectively on the weight of the composition (B), wherein the composition (B) preferably contains water and has a pH value in the range from about 2.5 to about 6.5, preferably from about 3.0 to about 5.5, particularly preferably from about 3.5 to about 5.0, in each case measured at 20° C., III. Mixing the compositions (A) and (B) with one another, preferably in a weight ratio (A):(B) in the range of from about 1:0.8 to about 1:2.5, preferably from about 1:1 to about 1:2, directly afterwards IV. Applying the mixture of (A) and (B) to the keratin fibers, in particular to human hair, and V. Rinsing after an exposure time of from about 0.1 to about 60 minutes, preferably from about 1 to about 45 minutes, more preferably from about 10 to about 30 minutes, VI. optionally further hair treatments, such as shaping, conditioning and/or drying.

Oxidation Dye Precursors

Among the oxidation dye precursors are oxidation dye precursors of the developer type and the coupler type. Particularly suitable oxidation dye precursors of the developer type are selected from at least one compound from the group of p-phenylenediamine, p-toluenediamine, 2-(2-hydroxyethyl)-p-phenylenediamine, 2-(1,2-dihydroxyethyl) p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis (2,5-diamino-phenyl)-1,4,7,10-tetraoxadecane, p-aminophenol, 4-amino-3-methylphenol, 4-amino-2-amino-methylphenol, 4-amino-2-(1,2-dihydroxyethyl) phenol, 4-amino-2-(diethylaminomethyl) phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazole-1-one and their physiologically compatible salts. Particularly preferred developer components are selected from p-toluenediamine, 2-(2-hydroxyethyl)-p-phenylenediamine, N,N-bis-(2-hydroxyethyl)-p-phenylenediamine, 2-methoxymethyl-p-phenylenediamine and/or 4,5-diamino-1-(2-hydroxyethyl)-pyrazole and their physiologically acceptable salts, and mixtures thereof.

Particularly suitable oxidation dye precursors of the coupler type are selected from the group of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy) ethanol, 1,3-bis(2,4-diaminophenoxy) propane, 1-methoxy-2-amino-4-(2-hydroxyethylamino) benzene (2-amino-4-[(2-hydroxyethyl) amino]anisole), 1,3-bis(2,4-diaminophenyl) propane, 2,6-bis(2'-hydroxyethylamino)-1-methylbenzene, 2-({3-[(2-hydroxyethyl)amino]-4-methoxy-5-methyl-phenyl}amino) ethanol, 2-({3-[(2-hydroxyethyl)amino]-2-methoxy-5-methylphenyl}amino) ethanol, 2-({3-[(2-hydroxyethyl) amino]-4,5-dimethylphenyl}amino) ethanol, 2-[3-morpholin-4-ylphenyl)amino]ethanol, 3-amino-4-(2-methoxyethoxy)-5-methylphenyl amine, 1-amino-3-bis-(2-hydroxyethyl)aminobenzene, resorcinol, 2-methylresorcinol, 4-chloro resorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyphenol, 7-hydroxyindole, 4-hydroxyindoline, 6-hydroxyindoline, 7-hydroxyindoline or mixtures of these compounds or physiologically acceptable salts thereof. Particularly preferred coupler components are selected from 3-aminophenol, 5-amino-2-methylphenol, 3-amino-2-chloro-6-methylphenol, 2-hydroxy-4-aminophenoxyethanol, 2-(2,4-diaminophenoxy) ethanol, 1-methoxy-2-amino-4-(2-hydroxyethylamino) benzene (2-amino-4-[(2-hydroxyethyl) amino]anisole), resorcinol, 2-methylresorcinol, 4-chlororesorcinol, 2-amino-3-hydroxypyridine, and their physiologically acceptable salts, as well as mixtures thereof.

In a preferred embodiment, the coloring agents as contemplated herein contain one or more oxidation dye precursors in a total amount of from about 0.001 to about 5.0% by weight, preferably from about 0.01 to about 4.0% by weight, further preferably from about 0.2 to about 3.5 by weight, further preferably from about 0.3 to about 2.5% by weight and very particularly preferably from about 0.7 to about 1.8% by weight, based on the weight of the coloring agent as contemplated herein or the weight of the composition (A) as contemplated herein.

In a preferred embodiment, the coloring agents as contemplated herein contain one or more oxidation dye precursors selected from at least one developer component and optionally at least one coupler component in a total amount of from about 0.001 to about 5.0% by weight, preferably from about 0.01 to about 4.0% by weight, further preferably from about 0.2 to about 3.5% by weight, further preferably from about 0.3 to about 2.5% by weight and very particularly preferably from about 0.7 to about 1.8% by weight, based on the weight of the coloring agent as contemplated herein or the weight of the composition (A) as contemplated herein.

Direct Acting

Instead of oxidation dye precursors or in addition thereto, the coloring agents as contemplated herein or the compositions A used in the method as contemplated herein can contain at least one direct dye. These are dyes which are directly applied to the hair and do not require an oxidative process to form the color. Direct dyes are usually nitrophenylenediamines, nitroaminophenols, azo dyes, anthraquinones or indophenols.

Direct dyes can be divided into anionic, cationic and nonionic direct dyes. The direct dyes are preferably selected from the nitrophenylenediamines, the nitroaminophenols, the azo dyes, the anthraquinones, the triarylmethane dyes or the indophenols and their physiologically compatible salts. The direct dyes are preferably contained in a total amount of from about 0.001 to about 2% by weight, based on the weight of the coloring agent as contemplated herein or the composition A as contemplated herein. Direct dyes are used in oxidative coloring agents to nuance the shade obtained, in oxidative bleaching agents to compensate for undesired reddish tones that may occur during degradation of the hair's own melanin.

Preferred anionic direct dyes are those compounds known under the international designations and trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol Blue and Tetrabromophenol Blue.

Preferred cationic direct dyes are cationic triphenylmethane dyes, for example Basic Blue 7, Basic Blue 26, Basic Violet 2 and Basic Violet 14, aromatic systems which are substituted by a quaternary nitrogen group, such as Basic Yellow 57, Basic Red 76, Basic Blue 99, Basic Brown 16 and Basic Brown 17, cationic anthraquinone dyes, such as HC Blue 16 (Bluequat B), and direct dyes that have a heterocycle having at least one quaternary nitrogen atom, in particular Basic Yellow 87, Basic Orange 31 and Basic Red 51. The cationic direct dyes which are marketed under the Arianor trademark are likewise preferred cationic direct dyes as contemplated herein.

Suitable nonionic direct dyes are, in particular, nonionic nitro- and quinone dyes and neutral azo dyes. Preferred nonionic direct dyes are those compounds known under the international names and trade names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis(2-hydroxyethyl)-amino-2-nitrobenzene, 3-nitro-4-(2-hydroxyethyl)aminophenol, 2-(2-hydroxyethyl)amino-4,6-dinitro-phenol, 4-[(2-hydroxyethyl)amino]-3-nitro-1-methylbenzene, 1-amino-4-(2-hydroxyethyl)amino-5-chloro-2-nitrobenzene 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and the like salts, 2-amino-6-chloro-4-nitrophenol, 4-ethylamino-3-nitrobenzoic acid and 2-chloro-6-ethylamino-4-nitrophenol.

Dicarboxylic Acids

The coloring agent as contemplated herein or the composition A used in the method as contemplated herein contains at least one dicarboxylic acid having 2 to 10 carbon atoms and/or at least one salt of these acid(s) in a total amount of from about 0.1 to about 5% by weight, calculated respectively on the undissociated dicarboxylic acid and based on the weight of the coloring agent or composition A.

Suitable dicarboxylic acids having 2 to 10 carbon atoms are selected from succinic acid, DL-malic acid, L-malic acid, D-malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, tauric acid, alpha-ketoglutaric acid, beta-ketoglutaric acid, oxal-acetic acid, and mixtures thereof.

Preferred dicarboxylic acids having 2 to 10 carbon atoms as contemplated herein are selected from dicarboxylic acid, L-tartaric acid, D-tartaric acid, L-tartaric acid, meso-tartaric acid, tartaric acid, as well as mixtures of these acids. As contemplated herein, succinic acid and DL-malic acid and salts thereof are particularly preferred. Extremely preferred as contemplated herein is succinic acid or at least a salt of succinic acid. The dicarboxylic acids mentioned make a significant contribution to the reduced hair damage by the coloring agents and dyeing methods as contemplated herein.

Depending on the pH value of the coloring agent as contemplated herein or the compositions used in one of the dyeing methods as contemplated herein, the at least one dicarboxylic acid having 2 to 10 carbon atoms is present as undissociated acid, partially dissociated or completely dissociated. If the at least one dicarboxylic acid having 2 to 10 carbon atoms is partially dissociated or completely dissociated, the counterion is selected from physiologically compatible cations, such as, in particular, the alkali metal, alkaline earth metal and zinc ions, as well as ammonium ions, alkylammonium, alkanolammonium and glucammonium ions, in particular mono-, di- and trimethyl-, ethyl- and hydroxyethylammonium ions. Preference is also given to the salts of saturated dicarboxylic acids having 2 to 10 carbon atoms with amino-$C_1$-$C_6$-alkanols, in particular with monoethanolamine, and amino-$C_1$-$C_6$-alkanediols, in particular with 2-amino-2-methylpropan-1-ol, 2-amino-2-methylpropane-1,3-diol, 2-amino-1-ol, 3-amino-propan-1-ol, 1-aminopropan-2-ol (MIPA) and 2-amino-2-(hydroxymethyl)-1,3-diol (TRIS), wherein the salts with monoethanolamine, 2-amino-2-methylpropan-1-ol and 2-amino-2-methylpropane-1,3-diol are particularly preferred.

Extraordinarily preferred are sodium, potassium, magnesium, calcium, ammonium and monoethanolammonium ions as counterions for the partially or completely dissociated dicarboxylic acids having 2 to 10 carbon atoms. However, neutralized dicarboxylic acids having 2 to 10 carbon atoms can also be used with alkaline reacting amino acids, for example arginine, lysine, ornithine and histidine.

The sodium, potassium, ammonium, monoethanolammonium, lysine and arginine salts and mixtures thereof are preferred salts of dicarboxylic acids having from 2 to 10 carbon atoms.

Preferred coloring agents as contemplated herein or preferred compositions A used as contemplated herein contain at least one dicarboxylic acid having 2 to 10 carbon atoms which is preferably selected from succinic acid, DL-malic acid, L-malic acid, D-malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, tauric acid, alpha-ketoglutaric acid, beta-ketoglutaric acid, oxalacetic acid, and mixtures thereof or one or more salts thereof in a total amount of from about 0.2 to about 4% by weight, preferably from about 0.33 to about 3% by weight, particularly preferably from about 0.5 to about 2% by weight, extremely preferably from about 1 to about 1.5% by weight, calculated respectively on the undissociated dicarboxylic acid and based on the weight of the coloring agent or based on the weight of the composition A as contemplated herein.

Even if the dicarboxylic acids are in salt form, the above amounts refer to the respective dicarboxylic acid in undissociated form, in order not to distort the quantity indicated by different molar weights of the salt forming counterions.

Very particularly preferred coloring agents as contemplated herein or particularly preferred compositions A used as contemplated herein contain, calculated respectively on the undissociated dicarboxylic acid and based on the weight of the coloring agent or composition A, from about 0.1 to about 5% by weight, preferably from about 0.2 to about 4 by weight, further preferably from about 0.33 to about 3% by weight, particularly preferably from about 0.5 to about 2% by weight, of succinic acid.

Further particularly preferred coloring agents as contemplated herein or particularly preferred compositions A used as contemplated herein contain, calculated respectively on the undissociated dicarboxylic acid and based on the weight of the coloring agent or composition A, from about 0.1 to about 5% by weight, preferably from about 0.2 to about 4% by weight, further preferably from about 0.33 to about 3% by weight, particularly preferably from about 0.5 to about 2% by weight, of DL-malic acid.

Keratin Hydrolyzate

The coloring agent as contemplated herein or the composition A used in the method as contemplated herein furthermore contains at least one keratin hydrolyzate with an average mean molecular weight Mw in the range from about 2000 to about 7000 daltons, preferably in the range from about 3000 to about 5000 daltons. The average molecular weight Mw of the at least one keratin hydrolyzate can be determined, for example, by gel permeation chromatography (GPC) with polystyrene as an internal standard in accordance with DIN 55672-3, version August 2007.

As contemplated herein, suitable keratin hydrolysates are derived from mammalian hair, in particular from the wool of sheep, goats, angora rabbits, lamas and alpacas, camel hair, furthermore finger and toe nails, claws, claws, hoof horns, beaks, feathers and horn scales. As contemplated herein, preferred keratin hydrolysates are derived from sheep wool.

Surprisingly, it has been determined that a keratin hydrolyzate having an average molecular weight Mw in the range from about 2000 to about 7000 daltons, preferably in the range from about 3000 to about 5000 daltons, is able to compensate the caused shifting of the targeted dyeing to darker nuances or the deterioration of the brightening performance of an oxidative hair coloring agent through the content of dicarboxylic acid(s) with 2 to 10 carbon atoms, optionally in combination with at least one basic amino acid selected from arginine, lysine and histidine.

Preferred coloring agent as contemplated herein or preferred compositions A used as contemplated herein contain the at least one keratin hydrolyzate having an average molecular weight Mw in the range from about 2000 to about 7000 daltons, preferably in the range from about 3000 to about 5000 daltons, in a total amount of from about 0.05 to about 4% by weight, preferably from about 0.1 to about 3% by weight, particularly preferably from about 0.4 to about 2.5% by weight, extremely preferably from about 0.7 to about 1.5% by weight, further extremely preferably from about 0.9 to about 1.3% by weight, based respectively on the weight of the coloring agent as contemplated herein or on the weight of the composition A as contemplated herein.

Further preferred coloring agents as contemplated herein or preferred compositions A used as contemplated herein contain at least one keratin hydrolyzate obtained from sheep wool having an average molecular weight Mw in the range from about 2000 to about 7000 daltons, preferably in the range from about 3000 to about 5000 daltons, in a total amount of from about 0.05 to about 4% by weight, preferably from about 0.1 to about 3% by weight, particularly preferably from about 0.4 to about 2.5% by weight, extremely preferably from about 0.7 to about 1.5% by weight, further extremely preferably from about 0.9-1.3% by weight, based respectively on the weight of the coloring agent as contemplated herein or on the weight of the composition A used as contemplated herein.

Water

The coloring agents as contemplated herein or compositions A used in the method as contemplated herein contain from about 20 to about 95% by weight of water. Preferred coloring agents or compositions A contain water from about 30 to about 90% by weight, particularly preferably from about 40 to about 85% by weight, extremely preferably from about 45 to about 75% by weight and in particular from about 55 to about 65% by weight, based respectively on the weight of the coloring agent as contemplated herein or to the weight of the composition A used as contemplated herein.

The coloring agents as contemplated herein or compositions A used in the method as contemplated herein contain from about 0 to less than about 0.1% by weight of peroxide compound(s). This feature limits the coloring agents as contemplated herein or compositions A used in the method as contemplated herein from the ready-to-use oxidative coloring compositions which are prepared by mixing a coloring agent as contemplated herein or a composition A as contemplated herein with an oxidizing agent.

Inventive coloring agents as contemplated herein or compositions A used as contemplated herein contain at least one amino acid selected from arginine, lysine, histidine or at least one of the salts of these amino acids. Mixtures of arginine and lysine are particularly preferred as contemplated herein. Among the preferred salts of arginine, lysine or histidine as contemplated herein are the ammonium salts, alkali metal salts and alkaline earth metal salts, in particular the lithium, sodium, potassium, magnesium and calcium salts, in addition the hydrohalides, in particular the hydrochlorides, and also the salts with at least one of the above-mentioned dicarboxylic acids having 2 to 10 carbon atoms, and mixtures of these salts. A particularly preferred amino acid salt as contemplated herein is lysine hydrochloride. The amino acids as contemplated herein, selected from arginine, lysine, histidine and their salts, can also contain water of crystallization.

As contemplated herein, particularly preferred coloring agents or particularly preferred compositions A as contemplated herein contain at least one amino acid selected from arginine, lysine, histidine or at least one salt of these amino acids, in a total quantity calculated on the mass of the free amino acids of from about 0.05-4% by weight of the free amino acid, preferably from about 0.1-3% by weight, particularly preferably from about 0.2-2% by weight, extremely preferably from about 0.3-1% by weight, based respectively on the weight of the coloring agent as contemplated herein or on the weight of composition A as contemplated herein.

The combination of succinic acid, lysine and arginine has proved to be particularly preferred as contemplated herein. The combination of succinic acid and arginine is also extremely preferred.

Particularly preferred coloring agents as contemplated herein contain succinic acid and/or an at least one succinic acid salt in a total quantity calculated on the mass of free dicarboxylic acid of from about 0.1 to about 5% by weight, preferably from about 0.2 to about 4% by weight, further preferably from about 0.33 to about 3% by weight, particularly preferably from about 0.5 to about 2% by weight, extremely preferably from about 1 to about 1.5% by weight, based respectively on the weight of the coloring agent or on the weight of the composition A used as contemplated herein, and also further at least one amino acid selected from arginine, lysine, or at least one salt of these amino acids, in a total amount calculated on the mass of free amino acid, of from about 0.05-4% by weight, preferably from about 0.1-3% by weight, particularly preferably from about 0.2-2% by weight, extremely preferably from about 0.3-1% by weight, based respectively on the weight of the coloring agent or composition A.

The combination of DL-malic acid, lysine and arginine has furthermore proven to be particularly preferred as contemplated herein. Also highly preferred is the combination of DL-malic acid and arginine.

As contemplated herein, particularly preferred coloring agents or particularly preferably used compositions A contain DL-malic acid and/or an at least one DL-malic acid salt in a total quantity calculated on the mass of free dicarboxylic acid of from about 0.1 to about 5% by weight, preferably from about 0.2 to about 4% by weight, further preferably from about 0.33 to about 3% by weight, particularly preferably from about 0.5 to about 2% by weight, extremely preferably from about 1 to about 1.5% by weight, based respectively on the weight of the coloring agent or by weight of the composition A, as well as at least one amino acid selected from arginine, lysine, histidine or at least one salt of these amino acids, in a total amount calculated on the mass of free amino acids of from about 0.05-4% by weight, preferably from about 0.1-3% by weight, particularly preferably from about 0.2-2% by weight, extremely preferably from about 0.3-1% by weight, based respectively on the weight of the coloring agent or composition A.

The coloring agent as contemplated herein or the composition A used in the method as contemplated herein preferably contains at least one alkalizing agent selected from ammonium hydroxide, monoethanolamine and sodium silicates, and mixtures thereof.

In order to achieve the desired durable dyeing of the keratin fibers, a coloring agent must have a pH in the range from about 6.5 to about 11.0, preferably from about 8 to about 10.5, particularly preferably from about 8.5 to about 10, in each case measured at 20° C. At these pH values, the outer layer of the keratin fibers opens optimally for the absorption of the oxidation dye precursors and the desired effect of the peroxide compound added unfolds optimally via the developer composition B.

Preferred coloring agent or compositions as contemplated herein or compositions A used in the method as contemplated herein have a pH value in the range from about 6.5 to about 11.0, preferably from about 8 to about 10.5, further preferably from about 8.5 to about 10, in each case measured at 20° C.

A particularly preferred alkalizing agent as contemplated herein is monoethanolamine.

In order to achieve a coloring method which is as free of odor as possible and to optimize the fastness properties of the dyeing, monoethanolamine is used in a total amount of from about 0.2-9% by weight, preferably from about 1-7% by weight, further preferably from about 1.5-6% % and particularly preferably from about 2 to about 4% by weight, based on the weight of the coloring agent as contemplated herein.

In addition to or instead of monoethanolamine, further preferred coloring agents as contemplated herein contain ammonium hydroxide, i.e., ammonia in the form of its aqueous solution. Appropriate aqueous ammonia solutions can be from about 10 to about 35 percent solutions (calculated in percent by weight, 100 g of aqueous ammonia solution containing accordingly, from about 10 to about 35 g of ammonia). Preference is given to using ammonia in the form of a from about 20 to about 30% strength by weight solution, particularly preferably in the form of a 25% strength by weight solution.

In a particularly preferred embodiment, the coloring agent as contemplated herein contains ammonium hydroxide in an amount of from about 0.20 to about 2.5% by weight, preferably from about 0.5 to about 2.0% by weight, further preferably from about 1.0 to about 1.5 by weight, and particularly preferably from about 0.31 to about 0.8% by weight, based on the weight of the coloring agent as contemplated herein.

In addition, other alkalizing agents, such as potassium hydroxide (KOH) and sodium hydroxide (NaOH), can preferably contain in a total amount of from about 0.05 to about 1.5% by weight, particularly preferably from about 0.1 to about 0.6% by weight, based respectively on the weight of the coloring agent as contemplated herein.

The coloring agent as contemplated herein or composition A used in the method as contemplated herein optionally contains further auxiliaries and additives. Thus, as contemplated herein, it has been found to be preferred when the coloring agent as contemplated herein contains at least one thickener. There are no fundamental restrictions with regard to these thickeners. Both organic and purely inorganic thickeners can be used.

As contemplated herein, preference is given to at least one polymeric organic thickener, preferably in a total amount of from about 0.01 to about 3% by weight, particularly preferably in a total quantity of from about 0.1 to about 1% by weight, extremely preferably in a total quantity of from about 0.2 to about 0.7% by weight, based respectively on the weight of the coloring agent as contemplated herein or the composition A as contemplated herein.

In a further preferred embodiment, the coloring agent as contemplated herein comprises at least one naturally occurring polymeric thickener which can be substituted by $C_1$-$C_6$-alkyl groups, $C_1$-$C_6$-hydroxyalkyl groups, carboxyalkyl groups, in particular carboxymethyl groups and/or quaternary ammonium or $C_1$-$C_6$-alkylammonium groups.

According to this embodiment, particularly preferred are biosaccharide gums of microbial origin, in particular xanthan gum, but also scleroglucangum, gums from plant exudates, such as gum arabic, ghatti gum, karaya gum, tragacanth gum, carrageenan gum, agar agar, guar gum, locust bean gum, pectins, alginates, starch, starch fractions and derivatives such as amylose, amylopectin and dextrins, cellulose derivatives such as methylcellulose, carboxyalkylcelluloses and hydroxyalkyl celluloses.

Preferred hydroxyalkylcelluloses are, in particular, the hydroxyethylcelluloses. Preferred carboxyalkylcelluloses are, in particular, the carboxymethylcelluloses.

Preference is also given to starch and its derivatives. Starch which is insoluble in cold water and forms a colloidal solution in boiling water can be obtained, for example, from potatoes, maize, rice, cassava, sweet potatoes, maras, grains, legumes such as peas and beans, bananas or the marrow of certain palm varieties Sagopalme). Natural starches derived from plants and/or chemically or physically modified starches can be used as contemplated herein. Modification can be achieved, for example, by introducing different functional groups on one or more of the hydroxyl groups of the starch. Usually, these are esters, ethers or amides of the starch with optionally substituted $C_1$-$C_{40}$ radicals. A corn starch etherified with a 2-hydroxypropyl group is particularly advantageous.

Preferred coloring agents as contemplated herein comprise xanthan gum, preferably from about 0.01 to about 3% by weight, particularly preferably from about 0.1 to about 1% by weight, extremely preferably from about 0.2 to about 0.7% by weight of xanthan gum, based respectively on the weight of the coloring agent as contemplated herein or the composition A as contemplated herein.

An emulsifier or a surfactant is also preferably added to the coloring agent or compositions (A) as contemplated herein, where surface-active substances are designated as surfactants or as emulsifiers, depending on the field of application, and are selected from anionic, cationic, zwitterionic, amphoteric and nonionic surfactants and emulsifiers. These substances are described in detail below.

Suitable anionic surfactants in preparations as contemplated herein are all anionic surface-active substances suitable for use on the human body. These are exemplified by a water-solubilizing, anionic group such as, for example, a carboxylate, sulfate, sulfonate or phosphate group and a lipophilic alkyl group having about 8 to 30 carbon atoms. In addition, glycol or polyglycol ether groups, ester, ether and amide groups as well as hydroxyl groups may be present in the molecule. Examples of suitable anionic surfactants are in each case in the form of the sodium, potassium and ammonium mono-, di- and trialkanol-ammonium salts with 2 to 4 carbon atoms in the alkanol group, linear and branched fatty acids having 8 to 30 carbon atoms (soaps), ether carboxylic acids of the formula $RO(CH_2CH_2O)xCH_2COOH$ in which R is a linear alkyl group with 8 to 30 carbon atoms and x=0 or 1 to 16, acylsarcosides having 8 to 24 carbon atoms in the acyl group, acyl taurides having 8 to 24 carbon atoms in the acyl group, acyl isethionates having 8 to 24 carbon atoms in the acyl group, sulfosuccinic acid mono- and dialkyl esters having 8 to 24 carbon atoms in the alkyl group and sulfosuccinic acid monoalkylpolyoxyethyl esters having 8 to 24 carbon atoms in the alkyl group and 1 to 6 oxyethyl groups, linear alkane sulfonates having 8 to 24 carbon atoms, linear olefin sulfonates having 8 to 24 carbon atoms, sulfonates of unsaturated fatty acids having 8 to 24 carbon atoms and 1 to 6 double bonds, sulfofatty acid methyl ester of fatty acids having 8 to 30 carbon atoms, alkyl sulfates and alkyl ether sulfates of the formula $RO(CH_2CH_2O)_xSO_3H$ in which R is a preferably linear alkyl group having 8 to 30 carbon atoms and x=0 or 1 to 12, mixtures of surface-active hydroxysulfonates, sulfated hydroxyalkylpolyethylene and/or hydroxyalkylenepropylene glycol ethers, esters of tartaric acid and citric acid with alcohols which are addition products of about 2-15 molecules of ethylene oxide and/or propylene oxide with fatty alcohols having 8 to 22 carbon atoms, alkyl and/or alkenyl ether phosphates of the formula

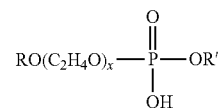

in which R is preferably an aliphatic, optionally unsaturated hydrocarbon radical having 8 to 30 carbon atoms, R' stands for hydrogen, a radical $(CH_2CH_2O)_yR$, and x and y are each independently a number from about 1 to about 10, sulfated fatty acid alkylene glycol esters of the formula $RC(O)O(alkO)_nSO_3H$ in which R is a linear or branched, aliphatic, saturated and/or unsaturated alkyl radical having 6 to 22 carbon atoms, alk stands for $CH_2CH_2$, $CHCH_3CH_2$ and/or $CH_2CHCH_3$ and N stands for a number from about 0.5 to about 5, monoglyceride sulfates and monoglyceride ether sulfates.

Preferred anionic surfactants are alkyl sulfates, alkyl ether sulfates and ether carboxylic acids having 10 to 18 carbon atoms in the alkyl group and up to 12 glycol ether groups in the molecule.

Zwitterionic surfactants are surface-active compounds which carry at least one quaternary ammonium group and at least one carboxylate, sulfonate or sulfate group in the molecule. Particularly suitable zwitterionic surfactants are the so-called betaines such as the N-alkyl-N,N-dimethylammonium glycinates, for example the cocoalkyldimethylammoniumglycinate, N-acylaminopropyl-N,N-dimethylammoniumglycinates, for example the cocoacylaminopropyldimethylammoniumglycinate, and 2-Alkyl-3-carboxymethyl-3-hydroxyethylimidazolines each having 8 to 18 carbon atoms in the alkyl or acyl group, and the cocoacylaminoethylhydroxyethylcarboxymethylglycinate. A preferred zwitterionic surfactant is the fatty acid amide derivative known under the INCI name Cocamidopropyl Betaine.

Amphoteric surfactants are those surface-active compounds which, in addition to a $C_8$-$C_{24}$-alkyl or acyl group, contain at least one free amino group and at least one —COOH or —SO3H group in the molecule and are capable of forming internal salts. Examples of suitable amphoteric surfactants are N-alkylglycines, N-alkylpropionic acids, N-alkyl-aminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each having from about 8 to about 24 carbon atoms in the alkyl group. Particularly preferred amphoteric surfactants are N-cocoalkylaminopropionate, coco-acylaminoethylaminopropionate and $C_{12}$-$C_{18}$-acyl sarcosine.

Furthermore, it has proved to be advantageous if the coloring agents as contemplated herein contain further nonionic surfactants. Nonionic surfactants contain as a hydrophilic group, for example, a polyol group, a polyalkylene glycol ether group or a combination of polyol and polyglycol ether groups. Such compounds are, for example,

- additive products of from 1 to about 50 moles of ethylene oxide and/or from 0 to about 5 moles of propylene oxide with linear and branched fatty alcohols having 8 to 30 carbon atoms, for example lauryl, myristyl, cetyl, but also stearyl, isostearyl and oleyl alcohol, of fatty acids having 8 to 30 carbon atoms and of alkylphenols having 8 to 15 carbon atoms in the alkyl group,
- with a methyl or $C_2$-$C_6$-alkyl radical, end-capped adducts of from 1 to about 50 moles of ethylene oxide and/or from 0 to about 5 moles of propylene oxide with linear and branched fatty alcohols having 8 to 30 carbon atoms, with fatty acids having 8 to 30 carbon atoms, and of alkylphenols having 8 to 15 carbon atoms in the alkyl group,
- polyglycerol esters and alkoxylated polyglycerol esters such as, for example, poly(3)glycerol diisostearate and poly(2)glycerol polyhydroxystearate,
- higher-alkoxylated, preferably propoxylated and, in particular, ethoxylated mono-, di- and triglycerides, such as, for example, PEG-20-glycerol monolaurate and PEG-20-glycerol monostearate,
- amine oxides,
- hydroxy mixed ethers,
- sorbitan fatty acid esters and addition products of ethylene oxide onto sorbitan fatty acid esters, for example the polysorbates, in particular PEG-20 sorbitan monolaurate,
- sugar fatty acid esters and addition products of ethylene oxide to sugar fatty acid esters,
- addition products of ethylene oxide to fatty acid alkanolamides and fatty amines,
- fatty acid N-alkylglucamides,
- alkylpolyglycosides corresponding to the general formula RO—$(Z)_x$, wherein R stands for alkyl, Z stands for sugar and x stands for the number of the sugar units.

In a preferred embodiment, the coloring agents of the invention or the compositions (A) used as contemplated herein contain at least one anionic, nonionic, zwitterionic or amphoteric surfactant in a total amount of from about 0.5 to about 20% by weight, preferably from about 1.5 to about 15% by weight, and very particularly preferably from about 3 to about 10% by weight, based on the weight of the coloring agent as contemplated herein or the composition (A) as contemplated herein.

Also preferred as contemplated herein are cationic surfactants of the quaternary ammonium compound type, esterquats and amidoamines. Preferred quaternary ammonium compounds are ammonium halides, in particular chlorides and bromides, such as alkyltrimethylammonium chlorides, dialkyldimethylammonium chlorides and trialkylmethylammonium chlorides, for. example, cetyltrimethylammonium chloride, stearyltrimethylammonium chloride, distearyldimethylammonium chloride, lauryldimethylammonium chloride, lauryldimethylbenzylammonium chloride and tricetylmethyl ammonium chloride, as well as those imidazolium compounds known under the INCI names Quaternium-27 and Quaternium-83. The long alkyl chains of the abovementioned surfactants preferably have 10 to 18 carbon atoms. Other cationic surfactants which can be used as contemplated herein are the quaternized protein hydrolysates.

The alkylamidoamine are usually prepared by amidation of natural or synthetic fatty acids and fatty acid cuts with dialkylaminoamines and are exemplified by a good conditioning effect particularly by their good biodegradability. A particularly suitable compound of this substance group as contemplated herein is the stearamidopropyldimethylamine.

Quaternary ester compounds, so-called esterquats, are also very readily biodegradable. Esterquats are known substances which contain both at least one ester function and at least one quaternary ammonium group as a structural element. Preferred esterquats are quaternized ester salts of fatty acids with triethanolamine, quaternized ester salts of fatty acids with diethanol alkylamines and quaternized ester salts of fatty acids with 1,2-dihydroxypropyl. N,N-bis(2-palmitoyloxyethyl) dimethylammonium chloride is an example of such esterquats.

In a further preferred embodiment, the coloring agents of the invention or the compositions (A) used as contemplated herein contain at least one cationic surfactant in a total amount of from about 0.01 to about 10% by weight, preferably from about 0.1 to about 6% by weight and very preferably from about 0.5 to about 3% by weight, based on the weight of the coloring agent as contemplated herein or the composition (A) as contemplated herein.

In a preferred embodiment, nonionic, zwitterionic and/or amphoteric surfactants and mixtures thereof may be preferred. The selection of these additional substances will be made by a person skilled in the art according to the desired properties of the agent.

Further preferred coloring agents as contemplated herein or compositions (A) as contemplated herein preferably contain at least one oil.

Preferably, at least is an oil in a total amount from from about 0.1-70% by weight, further preferably from about 1-50% by weight, extremely preferably of from about 3-10% by weight, based respectively on the weight of the coloring agent of the invention or the composition (A) as contemplated herein.

Particularly preferred oils as contemplated herein are selected from the esters of linear or branched saturated or unsaturated fatty alcohols with 2 to 30 carbon atoms with linear or branched saturated or unsaturated fatty acids having 2 to 30 carbon atoms which may be hydroxylated. These include cetyl 2-ethylhexanoate, 2-hexyldecyl stearate, 2-hexyldecyl laurate, isodecyl neopentanoate, isononyl isononanoate, 2-ethylhexyl palmitate and 2-ethylhexyl stearate. Also preferred are isopropyl myristate, isopropyl palmitate, isopropyl stearate, isopropyl isostearate, isopropyloleate, isooctyl stearate, isononyl stearate, isocetyl stearate, isononyl isononanoate, isotridecyl isononanoate, cetearyl isononanoate, 2-ethylhexyl laurate, 2-ethylhexylisostearate, 2-ethylhexyl cocoate, 2-octyldodecyl palmitate, butyloctanoate-2-butyloctanoate, diisotridecyl acetate, n-butyl stearate, n hexyl laurate, n decyloleate, oleyl oleate, oleyl erucate, erucyl oleate, erucyl erucate, ethylene glycol diolate and ethylene glycol dipalmitate.

Other preferred oils as contemplated herein are selected from natural and synthetic hydrocarbons, particularly preferably from mineral oils, paraffin oils, $C_{18}$-$C_{30}$ isoparaffins, in particular isoeicosan, polyisobutenes and polydecenes which are known, for example, under the name Emery 3004, 3006, 3010 or under the name ethylflovone albemarle or Nexbase 2004G from Nestle, furthermore selected from $C_8$-$C_{16}$ isoparaffins, in particular from isodecane, isododecane, isotetradecane and isohexadecane, and mixtures thereof, and 1,3-di-(2-ethylhexyl) cyclohexane.

Further preferred oils as contemplated herein are selected from the benzoic acid esters of linear or branched C8-22 alkanols. Particular preference is given to benzoic acid $C_{12}$-$C_{15}$-alkyl esters, benzoic acid isostearyl esters, ethylhexyl benzoate and benzoic acid octyl dodecyl esters.

Further preferred oils as contemplated herein are selected from fatty alcohols with 6-30 carbon atoms, which are unsaturated or branched and saturated or branched and unsaturated. The branched alcohols are frequently also referred to as Guerbet alcohols, since they are obtainable by the Guerbet reaction. Preferred alcohol oils are 2-hexyldecanol, 2-octyldodecanol, 2-ethylhexyl alcohol and isostearyl alcohol.

Further preferred oils are selected from mixtures of Guerbet alcohols and Guerbet alcohol esters, e.g., mixtures of 2-hexyldecanol and 2-hexyldecyl laurate.

Further preferred cosmetic oils as contemplated herein are selected from the triglycerides (=triple esters of glycerol) of linear or branched, saturated or unsaturated, optionally hydroxylated C8-30 fatty acids. Particular preference is given to the use of natural oils, e.g. amaranth oil, apricot kernel oil, argan oil, avocado oil, babassu oil, cottonseed oil, borage seed oil, camelina oil, thistle oil, peanut oil, pomegranate kernel oil, grapefruit seed oil, hemp oil, hazelnut oil, locust seed oil, jojoba oil, linseed oil, macadamian nut oil, corn oil, almond oil, marilla oil, evening primrose oil, olive oil, palm oil, palm kernel oil, paranut oil, pecan oil, peach kernel oil rape seed oil, castor oil, sanddorn fruit oil, sand kernel oil, sesame oil, soybean oil, sunflower oil, grape seed oil, walnut oil, wild rose oil, wheat germ oil, and the liquid fractions of coconut oil and the like. However, synthetic triglyceride oils, in particular capric/caprylic triglycerides, for example the commercial products Myritol® 318, Myritol® 331 (BASF) or Miglyol® 812 (Hills), with unbranched fatty acid residues and glyceryl triisosarin with branched fatty acid residues, are also preferred.

Further particularly preferred cosmetic oils as contemplated herein are selected from the dicarboxylic acid esters of linear or branched $C_2$-$C_{10}$-alkanols, in particular diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Further preferred cosmetic oils as contemplated herein are selected from the addition products of from about 1 to about 5 propylene oxide units to monohydric or polyhydric C8-22 alkanols such as octanol, decanol, decanediol, lauryl alcohol, myristyl alcohol and stearyl alcohol, e.g., PPG-2 myristyl ether and PPG-3 myristyl ether.

Further preferred cosmetic oils as contemplated herein are selected from the addition products of at least 6 ethylene oxide units and/or propylene oxide units to mono- or polyhydric C3-22 alkanols such as glycerol, butanol, butanediol, myristyl alcohol and stearyl alcohol which may be esterified if desired, e.g., PPG-14-butyl ether, PPG-9-butyl ether, PPG-10-butanediol, PPG-15 stearyl ether and glycereth-7-diisononanoate.

Further preferred cosmetic oils as contemplated herein are selected from the $C_8$-$C_{22}$ fatty alcohol esters of monovalent or polyvalent $C_2$-$C_7$-hydroxycarboxylic acids, in particular the esters of glycolic acid, lactic acid, malic acid, tartaric acid, citric acid and salicylic acid.

Further preferred cosmetic oils as contemplated herein are selected from the symmetrical, unsymmetrical or cyclic esters of carbonic acid with C3-22 alkanols, C3-22-alkanediols or C3-22 alkanetriols, e.g., dicaprylyl carbonate or the esters according to the teaching of DE 19756454 A1, in particular glycerin carbonate.

Further cosmetic oils which may be preferred as contemplated herein are selected from the esters of dimeric unsaturated $C_{12}$-$C_{22}$ fatty acids (dimer fatty acids) with monovalent linear, branched or cyclic $C_2$-$C_{18}$-alkanols or with polyhydric linear or branched $C_2$-$C_6$-alkanols.

Further cosmetic oils which are suitable as contemplated herein are selected from the silicone oils, which include, e.g., dialkyl- and alkylarylsiloxanes, such as cyclopentasiloxane, cyclohexasiloxane, dimethylpolysiloxane and methylphenylpolysiloxane, but also hexamethyldisiloxane, octamethyltrisiloxane and decamethyltetrasiloxane. Preference may be given to volatile silicone oils which may be cyclic, such as, e.g., octamethylcyclotetrasiloxane, decamethylcyclopentasiloxane and dodecamethylcyclohexasiloxane, and mixtures thereof, which are, e.g., contained in the commercial products DC 244, 245, 344 and 345 from Dow Corning. Also suitable are volatile linear silicone oils, in particular hexamethyldisiloxane (L2), octamethyltrisiloxane (L3), decamethyltetrasiloxane (L4), and any two or three mixtures of L2, L3 and/or L4, preferably mixtures such as those, for example, in the commercial products DC 2-1184, Dow Corning® 200 (0.65 cSt), and Dow Corning® 200 (1.5 cSt) from Dow Corning. Preferred non-volatile silicone oils are selected from higher molecular weight linear dimethylpolysiloxanes, commercially available, e.g., under the name Dow Corning® 190, Dow Corning® 200 fluid with kinematic viscosities (25° C.) in the range from from about 5-100 cSt, preferably from about 5-50 CSt or also from about 5-10 cSt, and dimethylpolysiloxane with a kinematic viscosity (25° C.) of about 350 cSt. It can be extremely preferred as contemplated herein to use mixtures of the abovementioned oils.

Preferred dyeing methods with the above-mentioned coloring agents or the compositions (A) and (B) as contemplated herein are exemplified in that the composition (B) is an oxidation composition that contains water and has a pH in the range of from about 2.5 to about 6, preferably from about 3.0 to about 5.5, particularly preferably from about 3.5 to about 5.0, in each case measured at 20° C., wherein the water content is preferably, respectively based on the weight of the composition (B), from about 40 to about 96% by weight, preferably from about 70-93% by weight, particularly preferably from about 80-90% by weight.

Further preferred dyeing methods as contemplated herein with the abovementioned coloring agent or the compositions (A) and (B) are exemplified in that the composition (B) contains from about 1 to about 23% by weight, further preferably from about 2.5 to about 21% by weight, particularly preferably from about 4 to about 20% by weight, very particularly preferably from about 5 to about 18% by weight and extraordinarily preferably from about 6 to about 12% by weight of hydrogen peroxide (calculated as 100% $H_2O_2$), based respectively on the weight of the composition (B), Oxidative compositions (B) particularly preferably used as contemplated herein further contain at least one oil in a total amount of from about 0.1 to about 60% by weight, particularly preferably from about 0.5 to about 40% by weight, extraordinarily preferably from about 2 to about 24% by weight, in each case based on the weight of the oxidation composition (B) preferably used as contemplated herein. The oils suitable for the oxidation compositions (B) used as contemplated herein are the same oils which are disclosed above as suitable oils for the coloring agents and compositions (A) as contemplated herein.

Fatty components preferably used as contemplated herein in the oxidation compositions (B) having a melting point in the range from about 23 to about 110° C. are selected from linear saturated 1-alkanols having 12-30 carbon atoms, preferably in a total amount of from about 0.1-8% particularly preferably from about 3 to about 6% by weight, based respectively on the weight of the oxidation composition (B) used as contemplated herein.

Preference is given to the at least one linear saturated 1-alkanol having 12-30 carbon atoms selected from lauryl alcohol, myristyl alcohol, cetyl alcohol, stearyl alcohol, arachidyl alcohol and behenyl alcohol, and mixtures of these 1-alkanols, particularly preferably cetyl alcohol, stearyl alcohol and cetyl alcohol/stearyl alcohol mixtures.

Oxidative compositions (B) preferably used as contemplated herein further contain, in each case based on their weight, at least one linear saturated 1-alkanol having 12-30 carbon atoms in a total amount of from about 0.1-8% by weight, preferably in a total quantity of from about 2-6% by weight, wherein at least one alkanol selected from cetyl alcohol, stearyl alcohol and cetyl alcohol/stearyl alcohol mixtures is contained.

Further oxidation compositions (B) as contemplated herein preferably contain at least one fat component with a melting point in the range from about 23 to about 110° C., which is selected from esters of a saturated monovalent $C_{16}$-$C_{60}$ alkanol and a saturated $C_8$-$C_{36}$ monocarboxylic acid, in particular cetyl behenate, stearylbehenate and $C_{20}$-$C_{40}$-alkyl stearate, glycerol esters of saturated linear $C_{12}$-$C_{30}$-carboxylic acids which may be hydroxylated, candelilla wax, carnauba wax, beeswax, saturated linear $C_{14}$-$C_{36}$-carboxylic acids, and mixtures of the abovementioned substances.

Further oxidation compositions (B) used as contemplated herein preferably contain at least one surfactant, preferably in a total amount of from about 0.5-10% by weight, preferably from about 1-5% by weight, based on the weight of the oxidation composition (B) used as contemplated herein. For the compositions (B), the same surfactants are suitable as those for the coloring agents as contemplated herein and compositions (A) as contemplated herein used above.

It has proved to be advantageous as contemplated herein if the weight ratio (A):(B) from the composition (A) as contemplated herein and the oxidizing composition (B) used as contemplated herein is in the range from about 1:0.8 to about 1:2.5, preferably from about 1:1 to about 1:2.

Preferred methods as contemplated herein for the oxidative dyeing of keratin fibers, in particular of human hair, with the coloring agent as contemplated herein or the composition (A) and the oxidation composition (B) are exemplified by a weight ratio (A):(B) is in the range of from about 1:0.8 to about 1:2.5, preferably from about 1:1 to about 1:2.

The effect as contemplated herein of the keratin hydrolyzate with an average molecular weight Mw in the range from about 2000 to about 7000 daltons, preferably in the range from about 3000 to about 5000 daltons, occurs in particular with bright and lightening color nuances. Such bright and lightening color nuances are exemplified on the one hand by the fact that the coloring agent or the composition (A) used as contemplated herein contains at least one oxidation dye precursor in a total amount of only from about 0.001 to about 0.3% by weight, preferably from about 0.01 to about 0.2% by weight, based on the weight of the composition (A), and the composition (B) contains from about 5 to about 18% by weight, preferably from about 6 to about 12% by weight, of hydrogen peroxide, based respectively on the weight of the composition (B), wherein the compositions (A) and (B) preferably are mixed together in a weight ratio (A):(B) in the range from about 1:0.8 to about 1:2.5, preferably from about 1:1 to about 1:2.

As contemplated herein, a method for the oxidative dyeing of keratin fibers, in particular of human hair, which comprises the following method steps, is particularly preferred I. Providing a composition (A) containing, based on its weight,
a) at least one compound selected from the group of oxidation dye precursors and direct dyes, and mixtures thereof,
b) at least one dicarboxylic acid having 2 to 10 carbon atoms and/or at least one salt of these acid(s) in a total quantity of from about 0.1 to about 5% by weight, calculated respectively on the undissociated dicarboxylic acid and based on the weight of the composition (A),
c) at least one keratin hydrolyzate having an average molecular weight Mw in the range from about 2000 to about 7000 daltons, preferably in the range from about 3000 to about 5000 daltons,
d) from about 20 to about 95% by weight of water and
e) zero to less than about 0.1% by weight of peroxide compound(s).

II. Providing a composition (B) containing at least one peroxide compound, which preferably is hydrogen peroxide in an amount of from about 1 to about 23% by weight, further preferably from about 2.5 to about 2% by weight, particularly preferably from about 4 to about 20% by weight, very particularly preferably from about 5 to about 18% by weight and most preferably from about 6 to about 12% by weight, based respectively on the weight of the composition (B),
wherein the composition (B) preferably contains water and has a pH value in the range from about 2.5 to about 6.5, preferably from about 3.0 to about 5.5, particularly preferably from about 3.5 to about 5.0, in each case measured at 20° C., III. Mixing the compositions (A) and (B) with one another, preferably in a weight ratio (A):(B) in the range of from about 1:0.8 to about 1:2.5, preferably from about 1:1 to about 1:2, directly afterwards IV. Applying the mixture of (A) and (B) to the keratin fibers, in particular to human hair, and V. Rinsing after an exposure time of from about 0.1 to about 60 minutes, preferably from about 1 to about 45 minutes, more preferably from about 10 to about 30 minutes, VI. Optionally further hair treatments, such as shaping, conditioning and/or drying.

Necessary changes having been made, the said preferred oxidative coloring agents as contemplated herein are valid for the preferred methods for the oxidative dyeing of keratin fibers as contemplated herein, in particular of human hair, with the coloring agent as contemplated herein or the composition (A) and the oxidation composition (B) and its preferred embodiments.

A further subject matter of the present disclosure provides for the use of a keratin hydrolyzate having an average molecular weight Mw in the range from about 2000 to about 7000 daltons, preferably in the range from about 3000 to about 5000 daltons, for reducing or preventing the loss in lifting performance or brightening performance, which is effected by the addition of at least one dicarboxylic acid having from about 2 to about 10 carbon atoms, optionally in combination with at least one basic amino acid selected from arginine, lysine and histidine, to an oxidative hair coloring agent, wherein the loss of the lifting performance or the brightening performance $\Delta L$, calculated according to the formula $\Delta L=((L_i-L_0)^2)^{1/2}$, is preferably at most about 1.5, particularly preferably at most about 0.9.

The oxidative coloring agents preferred as contemplated herein and the said preferred dyeing methods as contemplated herein are valid, necessary changes being made, for the application as contemplated herein.

Example Part

The following coloring agents or compositions (A) were prepared (oil-in-water emulsions, all amounts in % by weight) (E1*=as contemplated herein)

| Raw material | V1 | V2 | E1* |
|---|---|---|---|
| Xanthan gum | 0.1 | 0.1 | 0.1 |
| 2-octyldodecanol | 2.3 | 2.3 | 2.3 |
| Cetearyl alcohol | 18 | 18 | 18 |
| Glycerin monostearate | 6 | 6 | 6 |
| Glycerol 99.5% | 2 | 2 | 2 |
| Cocoamidopropyl | 0.8 | 0.8 | 0.8 |
| Monoethanolamine | 6 | 6 | 6 |
| 2-amino-2-methylpropanol | 0.1 | 0.1 | 0.1 |
| Sodium sulfite, anhydrous | 0.3 | 0.3 | 0.3 |
| Caramel syrup, 75% | 0.1 | 0.1 | 0.1 |
| Ascorbic acid | 0.1 | 0.1 | 0.1 |
| Succinic acid | — | 1.0 | 1 |
| L-lysine · HCl | — | 0.2 | 0.2 |
| L-arginine | — | 0.2 | 0.2 |
| Grapeseed oil | 1 | 1 | 1 |
| p-Toluylenediamine | 0.1 | 0.1 | 0.1 |
| Resorcinol | 0.02 | 0.02 | 0.02 |
| m-aminophenol | 0.003 | 0.003 | 0.003 |
| 4-chlororesorcinol | 0.03 | 0.03 | 0.03 |
| Keratin hydrolyzate having an average molecular weight Mw in the range from 3000 to 5000 daltons | — | — | 1.05 |
| Water, fully desalted | Ad 100 | Ad 100 | Ad 100 |

The fat base was melted together at 80° C. and dispersed with a portion of the water. Subsequently, the remaining formulation components were worked in in succession with stirring. The mixture was then filled up to 100% by weight with water and the formulation was stirred cold. The recipes V1 and V2 are comparative formulations without keratin hydrolyzate having an average molecular weight Mw in the range from 2000 to 7000 daltons. The formulation E1 is as contemplated herein.

Oxidizing Agent Preparation (B) (all Amounts in % by Weight)

| Raw material | (B) |
|---|---|
| Disodiumpyrophosphate | 0.1 |
| Dipicolinic acid | 0.1 |
| Potassium hydroxide 50% | 0.3 |
| 1-hydroxyethane-1,1-diphosphonic acid 60% | 0.25 |
| Fatty alcohol sulfate $C_{16}$-$C_{18}$ Sodium salt | 0.3 |
| PEG-40 Castor oil | 0.6 |
| Cetearyl alcohol | 3.6 |
| Ceteareth-20 | 0.5 |
| Beeswax | 0.3 |
| Isopropyl myristate | 10 |
| Hydrogen peroxide | 11.6 |
| Water demineralized | Ad 100 |

2. Reduced Loss in Lifting Performance (Brightening Ability) by the Addition of the Keratin Hydrolyzate with an Average Molecular Weight Mw in the Range from 2000 to 7000 Dalton To prepare the oxidative coloring agents for the determination of the brightening performance ("lifting performance"), the cosmetic compositions V1, V2 and E1 were each mixed in a weight ratio of 1:2 with the above oxidizing agent preparation (B).

The oxidative coloring agents prepared in this way were each applied in a defined amount (4 g of oxidative coloring agent per 1 g of yak hair) on yak hair strands (12 strands per oxidative coloring agent) and remained on the hair strands for 30 minutes at 32° C. Then, the remaining agents were each rinsed with lukewarm water from the hair strands for 2 minutes, the strands were first dried with a towel and then blown dry.

All strands were measured with a color measuring device from Datacolor, type Spectraflash 450. The values used for the assessment of the lifting performance or the brightening capacity are obtained from the L*a*b color measurement values measured on the respective strand as follows:

$$\Delta L = ((L_i - L_0)^2)^{1/2}$$

$L_0$ are in each case the mean values of the color measurement values of the yak hair strands colored using V1 from the 12 measurements. $L_i$ stands for in each case the mean values of the color measurement values which are obtained for colored yak hair strands using V2 or E1.

In the following tables, the ΔL values for the colorations using the coloring agent E1 as contemplated herein are shown in comparison with V1 and V2. The colorings with the cosmetic composition E1 as contemplated herein, which contains at least one keratin hydrolyzate having an average molecular weight Mw in the range from 2000 to 7000 daltons, preferably in the range from 3000 to 5000 daltons, in a total quantity of 1.05% by weight, only have a lower brightening performance 0.7, while the brightening performance of V1 to V2=1.7.

| Oxidative coloring agent mixture | L (lifting performance) |
|---|---|
| E1 + O1 (1:2) | 6.1 |
| V1 + O1 (1:2) | 6.8 |
| V2 + O1 (1:2) | 5.1 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A coloring agent for keratin fibers comprising, based on its weight,
   a) at least one compound selected from the group of oxidation dye precursors, direct dyes, or mixtures thereof,
   b) at least one dicarboxylic acid having 2 to 10 carbon atoms and/or at least one salt of this/these acid(s) in a total quantity of from about 0.1 to about 5% by weight, calculated respectively on the undissociated dicarboxylic acid and based on the weight of the coloring agent, c) at least one keratin hydrolyzate having an average molecular weight Mw in the range from about 2000 to about 7000 daltons,
d) from about 20 to about 95% by weight of water, and
e) from zero to less than about 0.1% by weight of peroxide compound(s).

2. The coloring agent according to claim 1, wherein the at least one dicarboxylic acid having 2 to 10 carbon atoms is selected from the group of succinic acid, DL-malic acid, L-malic acid, D-malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, tauric acid, alpha-ketoglutaric acid, beta-ketoglutaric acid, oxalacetic acid and mixtures thereof.

3. The coloring agent according to claim 1, wherein the at least one salt of the at least one dicarboxylic acid having 2 to 10 carbon atoms is selected from the group of sodium, potassium, magnesium, calcium, ammonium, and monoethanolammonium salts; the salts with arginine, lysine, ornithine and histidine; and mixtures of these salts.

4. The coloring agent according to claim 1, wherein the at least one dicarboxylic acid having 2 to 10 carbon atoms and/or its salt is contained in a total amount of from about 0.2 to about 4% by weight, calculated respectively on the undissociated dicarboxylic acid and based on the weight of the coloring agent.

5. The coloring agent according to claim 1, wherein the at least one keratin hydrolyzate is contained in a total quantity of from about 0.05-4% by weight, based respectively on the weight of the coloring agent.

6. The coloring agent according to claim 1, comprising water from about 30 to about 90% by weight, based respectively on the weight of the coloring agent.

7. The coloring agent according to claim 1, further comprising at least one amino acid chosen from the group of arginine, lysine, histidine, or mixtures thereof.

8. A method for the oxidative dyeing of keratin fibers comprising the following method steps:
I. Providing a composition (A) comprising, based on its weight,
    a) at least one compound selected from the group of oxidation dye precursors, direct dyes, and mixtures thereof,
    b) at least one dicarboxylic acid having 2 to 10 carbon atoms and/or at least one salt of these acid(s) in a total quantity of from about 0.1 to about 5% by weight, calculated respectively on the undissociated dicarboxylic acid and based on the weight of the composition (A),
    c) at least one keratin hydrolyzate having an average molecular weight Mw in the range from about 2000 to about 7000 daltons,
    d) from about 20 to about 95% by weight of water, and
    e) zero to less than about 0.1% by weight of peroxide compound(s),
II. Providing a composition (B) comprising at least one peroxide compound, in an amount of from about 1 to about 23% by weight, based respectively on the weight of the composition (B), wherein the composition (B) has a pH value in the range of from about 2.5 to about 6.5,
III. Mixing the compositions (A) and (B) with each other, directly afterward
IV. Applying the mixture of (A) and (B) to the keratin fibers, and
V. Rinsing after an exposure time of from about 0.1 to about 60 minutes.

9. The method according to claim 8, wherein the composition (A) is a coloring agent comprising, based on its weight,
    a) at least one compound selected from the group of oxidation dye precursors, direct dyes, or mixtures thereof,
    b) at least one dicarboxylic acid having 2 to 10 carbon atoms and/or at least one salt of this/these acid(s) in a total quantity of from about 0.1 to about 5% by weight, calculated respectively on the undissociated dicarboxylic acid and based on the weight of the coloring agent,
    c) at least one keratin hydrolyzate having an average molecular weight Mw in the range from about 2000 to about 7000 daltons,
    d) from about 20 to about 95% by weight of water, and
    e) from zero to less than about 0.1% by weight of peroxide compound(s).

10. The method according to claim 8, wherein the composition (A) comprises at least one oxidation dye precursor in a total amount of from about 0.001 to about 0.3% by weight, based on the weight of the composition (A), and the composition (B) comprises from about 5 to about 18% by weight, of hydrogen peroxide, based respectively on the weight of the composition (B).

11. The coloring agent according to claim 1, wherein the c) at least one keratin hydrolyzate has an average molecular weight Mw in the range from about 3000 to about 5000 daltons.

12. The coloring agent according to claim 1, wherein the at least one dicarboxylic acid having 2 to 10 carbon atoms is selected from the group of succinic acid, DL-malic acid, and mixtures thereof.

13. The coloring agent according to claim 1, wherein the at least one dicarboxylic acid having 2 to 10 carbon atoms and/or its salt is contained in a total amount of from about 0.5 to about 2% by weight, calculated respectively on the undissociated dicarboxylic acid and based on the weight of the coloring agent,
    wherein the c) at least one keratin hydrolyzate is contained in a total quantity of from about 0.9-1.3% by weight, based respectively on the weight of the coloring agent, and
    wherein water is present in an amount of from about 45 to about 75% by weight, based respectively on the weight of the coloring agent.

14. The coloring agent according to claim 7, wherein the at least one amino acid is chosen from mixtures of arginine and lysine.

15. The coloring agent according to claim 7, wherein the at least one amino acid is present in a total amount of from about 0.05 to about 3% by weight, based respectively on the undissociated amino acid and based on the weight of the coloring agent.

16. The coloring agent according to claim 7, wherein the at least one amino acid is present in a total amount of from about 0.2 to about 1.2% by weight, based on the undissociated amino acid and based on the weight of the coloring agent.

17. The method according to claim 8, comprising providing the composition (B) comprising the at least one peroxide compound, in an amount of from about 6 to about 12% by weight, based respectively on the weight of the composition (B), wherein the composition (B) further comprises water and has a pH value in the range of from about 3.5 to about 5.0, in each case measured at 20° C.

18. The method according to claim 8, comprising mixing the compositions (A) and (B) with each other in a weight ratio (A):(B) in the range of from about 1:0.8 to about 1:2.5.

19. The method according to claim 8, comprising rinsing after an exposure time of from about 10 to about 30 minutes.

20. The method according to claim 8, wherein the composition (A) comprises the at least one oxidation dye precursor in a total amount of from about 0.01 to about 0.2% by weight, based on the weight of the composition (A), and the composition (B) comprises from 6 to about 12% by weight of hydrogen peroxide, based respectively on the weight of the composition (B).

* * * * *